US008834361B2

(12) United States Patent  
Hashiba et al.

(10) Patent No.: US 8,834,361 B2  
(45) Date of Patent: Sep. 16, 2014

(54) SYSTEMS, DEVICES AND METHODS FOR ACCESSING A BODILY OPENING

(75) Inventors: Kiyoshi Hashiba, Sao Paulo (BR); Vihar C. Surti, Winston-Salem, NC (US); Kimberly K. Ingram, Rural Hall, NC (US); Andres F. Aguirre, Burlington, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 753 days.

(21) Appl. No.: 12/620,864

(22) Filed: Nov. 18, 2009

(65) Prior Publication Data  
US 2010/0292541 A1 Nov. 18, 2010

Related U.S. Application Data

(63) Continuation-in-part of application No. 12/466,866, filed on May 15, 2009.

(51) Int. Cl.  
*A61B 1/32* (2006.01)  
*A61B 17/34* (2006.01)  
*A61B 17/00* (2006.01)

(52) U.S. Cl.  
CPC ..... *A61B 17/3421* (2013.01); *A61B 2017/3425* (2013.01); *A61B 2017/3488* (2013.01); *A61B 2017/3419* (2013.01); *A61B 17/3431* (2013.01); *A61B 17/3478* (2013.01); *A61B 2017/00278* (2013.01); *A61B 2017/3484* (2013.01)  
USPC ............ 600/209; 600/206; 600/208; 600/217

(58) Field of Classification Search  
USPC .......... 600/206–209, 217; 606/198; 623/1.11, 623/1.12, 1.16, 1.17, 1.32, 1.33  
See application file for complete search history.

(56) References Cited

U.S. PATENT DOCUMENTS

| | | | |
|---|---|---|---|
| 2,313,164 A * | 3/1943 | Nelson ......................... | 600/208 |
| 3,774,608 A | 11/1973 | Wohler, Jr. | |
| 3,915,171 A | 10/1975 | Shermeta | |
| 4,023,559 A | 5/1977 | Gaskell | |
| 4,224,929 A | 9/1980 | Furihata | |
| 4,249,535 A | 2/1981 | Hargest, III | |
| 4,315,509 A | 2/1982 | Smit | |

(Continued)

FOREIGN PATENT DOCUMENTS

| | | |
|---|---|---|
| EP | 1062966 B1 | 1/2004 |
| EP | 1985226 A2 | 10/2008 |

(Continued)

OTHER PUBLICATIONS

International Search Report/Written Opinion for PCT/US2009/036173 mailed May 29, 2009.

(Continued)

*Primary Examiner* — Eduardo C Robert  
*Assistant Examiner* — Julianna N Harvey  
(74) *Attorney, Agent, or Firm* — Brinks Gilson & Lione

(57) ABSTRACT

Medical systems, devices and methods are provided for accessing a bodily opening that, among other things, are safe and reliable, and facilitate manipulation of a medical instrument. The medical access device generally includes an elongated flexible sheath and an expandable frame connected to the distal end of the flexible sheath. The sheath and expandable frame are operable between expanded and collapsed configurations to provide a pathway from a natural orifice to the bodily opening.

21 Claims, 11 Drawing Sheets

(56) References Cited

U.S. PATENT DOCUMENTS

| | | |
|---|---|---|
| 4,327,736 A | 5/1982 | Inoue |
| 4,538,606 A | 9/1985 | Whited |
| 4,664,114 A | 5/1987 | Ghodsian |
| 4,676,778 A | 6/1987 | Nelson, Jr. |
| 4,686,965 A | 8/1987 | Bonnet et al. |
| 4,765,314 A | 8/1988 | Kolditz et al. |
| 4,773,394 A | 9/1988 | Reichstein et al. |
| 5,002,532 A | 3/1991 | Gaiser et al. |
| 5,025,778 A | 6/1991 | Silverstein et al. |
| 5,158,543 A | 10/1992 | Lazarus |
| 5,197,971 A | 3/1993 | Bonutti |
| 5,217,001 A | 6/1993 | Nakao et al. |
| 5,279,565 A | 1/1994 | Klein et al. |
| 5,354,302 A | 10/1994 | Ko |
| 5,380,304 A | 1/1995 | Parker |
| 5,389,074 A | 2/1995 | Parker et al. |
| 5,400,770 A | 3/1995 | Nakao et al. |
| 5,443,498 A * | 8/1995 | Fontaine ............... 623/1.17 |
| 5,443,500 A * | 8/1995 | Sigwart ............... 623/1.17 |
| 5,707,355 A | 1/1998 | Zimmon |
| 5,814,073 A | 9/1998 | Bonutti |
| 5,846,182 A | 12/1998 | Wolcott |
| 5,876,325 A | 3/1999 | Mizuno et al. |
| 5,882,345 A | 3/1999 | Yoon |
| 5,906,579 A | 5/1999 | Vander Salm et al. |
| 6,030,365 A | 2/2000 | Laufer |
| 6,156,006 A | 12/2000 | Brosens et al. |
| 6,234,958 B1 | 5/2001 | Snoke et al. |
| 6,315,733 B1 | 11/2001 | Zimmon |
| 6,488,692 B1 | 12/2002 | Spence et al. |
| 6,511,491 B2 * | 1/2003 | Grudem et al. ............... 606/153 |
| 6,535,764 B2 | 3/2003 | Imran et al. |
| 6,551,270 B1 | 4/2003 | Bimbo et al. |
| 6,572,629 B2 | 6/2003 | Kalloo et al. |
| 6,652,492 B1 | 11/2003 | Bell et al. |
| 6,689,062 B1 | 2/2004 | Mesallum |
| 6,918,871 B2 | 7/2005 | Schulze |
| 6,984,244 B2 * | 1/2006 | Perez et al. ............... 623/1.23 |
| 6,988,987 B2 | 1/2006 | Ishikawa |
| 7,128,708 B2 | 10/2006 | Saadat et al. |
| 7,204,841 B2 | 4/2007 | Green |
| 7,273,451 B2 | 9/2007 | Sekine et al. |
| 7,575,548 B2 | 8/2009 | Takemoto et al. |
| 7,615,003 B2 | 11/2009 | Stefanchik et al. |
| 7,615,005 B2 | 11/2009 | Stefanchik et al. |
| 7,637,905 B2 | 12/2009 | Saadat et al. |
| 7,637,919 B2 | 12/2009 | Ishikawa et al. |
| 7,654,951 B2 | 2/2010 | Ishikawa |
| 7,717,847 B2 | 5/2010 | Smith |
| 7,721,742 B2 | 5/2010 | Kalloo et al. |
| 7,735,489 B2 | 6/2010 | Mikkaichi et al. |
| 7,785,251 B2 | 8/2010 | Wilk |
| 7,785,333 B2 | 8/2010 | Miyamoto et al. |
| 7,815,589 B2 | 10/2010 | Meade et al. |
| 7,815,591 B2 | 10/2010 | Levine et al. |
| 7,819,836 B2 | 10/2010 | Levine et al. |
| 2001/0049503 A1 | 12/2001 | Estabrook et al. |
| 2002/0022764 A1 | 2/2002 | Smith et al. |
| 2002/0022851 A1 | 2/2002 | Kalloo et al. |
| 2002/0193806 A1 | 12/2002 | Moenning et al. |
| 2003/0065359 A1 | 4/2003 | Weller et al. |
| 2003/0093104 A1 | 5/2003 | Bonner et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa |
| 2004/0249367 A1 | 12/2004 | Saadat et al. |
| 2005/0056292 A1 | 3/2005 | Cooper |
| 2005/0101837 A1 | 5/2005 | Kalloo et al. |
| 2005/0107664 A1 | 5/2005 | Kalloo et al. |
| 2005/0149078 A1 | 7/2005 | Vargas et al. |
| 2005/0251176 A1 | 11/2005 | Swanstrom et al. |
| 2005/0277945 A1 | 12/2005 | Saadat et al. |
| 2006/0015006 A1 | 1/2006 | Laurence et al. |
| 2006/0100480 A1 | 5/2006 | Ewers et al. |
| 2006/0135971 A1 | 6/2006 | Swanstrom et al. |
| 2006/0135984 A1 | 6/2006 | Kramer et al. |
| 2006/0135985 A1 | 6/2006 | Cox et al. |
| 2006/0178560 A1 | 8/2006 | Saadat et al. |
| 2006/0200004 A1 | 9/2006 | Wilk |
| 2006/0211919 A1 | 9/2006 | Wilk |
| 2006/0212063 A1 | 9/2006 | Wilk |
| 2006/0229653 A1 | 10/2006 | Wilk |
| 2006/0237022 A1 | 10/2006 | Chen et al. |
| 2006/0237023 A1 | 10/2006 | Cox et al. |
| 2006/0241344 A1 | 10/2006 | Wilk |
| 2006/0241480 A1 | 10/2006 | Wilk |
| 2006/0241570 A1 | 10/2006 | Wilk |
| 2006/0241651 A1 | 10/2006 | Wilk |
| 2006/0252997 A1 | 11/2006 | Wilk |
| 2006/0253123 A1 | 11/2006 | Wilk |
| 2006/0258909 A1 | 11/2006 | Saadat et al. |
| 2007/0038224 A1 | 2/2007 | Ortiz |
| 2007/0051380 A1 | 3/2007 | Pasricha |
| 2007/0106313 A1 | 5/2007 | Golden et al. |
| 2007/0163596 A1 | 7/2007 | Mikkaichi et al. |
| 2007/0167675 A1 | 7/2007 | Miyamoto et al. |
| 2007/0167676 A1 | 7/2007 | Miyamoto et al. |
| 2007/0167967 A1 | 7/2007 | Mikkaichi et al. |
| 2007/0260117 A1 | 11/2007 | Zwolinski et al. |
| 2008/0021277 A1 | 1/2008 | Stefanchik |
| 2008/0039786 A1 | 2/2008 | Epstein et al. |
| 2008/0051735 A1 | 2/2008 | Measamer et al. |
| 2008/0058650 A1 | 3/2008 | Saadat et al. |
| 2008/0097157 A1 | 4/2008 | Ortiz et al. |
| 2008/0119868 A1 | 5/2008 | Sharp et al. |
| 2008/0161644 A1 | 7/2008 | Ghabrial |
| 2008/0183039 A1 | 7/2008 | Long et al. |
| 2008/0228029 A1 | 9/2008 | Mikkaichi et al. |
| 2008/0249358 A1 | 10/2008 | Motai et al. |
| 2008/0249416 A1 | 10/2008 | Sato |
| 2008/0249474 A1 | 10/2008 | Baker |
| 2008/0255422 A1 | 10/2008 | Kondoh et al. |
| 2008/0255423 A1 | 10/2008 | Kondo et al. |
| 2008/0262294 A1 | 10/2008 | Ewers et al. |
| 2008/0262300 A1 | 10/2008 | Ewers |
| 2008/0262302 A1 | 10/2008 | Azarbarzin et al. |
| 2008/0287743 A1 | 11/2008 | Smith et al. |
| 2008/0287963 A1 | 11/2008 | Rogers et al. |
| 2008/0287983 A1 | 11/2008 | Smith et al. |
| 2008/0300547 A1 | 12/2008 | Bakos |
| 2008/0319258 A1 | 12/2008 | Thompson |
| 2009/0054728 A1 | 2/2009 | Trusty |
| 2009/0112062 A1 | 4/2009 | Bakos |
| 2009/0143643 A1 | 6/2009 | Weitzner et al. |
| 2009/0149714 A1 | 6/2009 | Bonadio |
| 2009/0192465 A1 | 7/2009 | Smith |
| 2009/0259141 A1 | 10/2009 | Ewers et al. |
| 2009/0259172 A1 | 10/2009 | Yamaoka et al. |
| 2009/0275798 A1 | 11/2009 | Naito |
| 2009/0275967 A1 | 11/2009 | Stokes et al. |
| 2009/0276055 A1 | 11/2009 | Harris et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0036200 A1 | 2/2010 | Okada |
| 2010/0042078 A1 | 2/2010 | Okada |
| 2010/0069716 A1 | 3/2010 | Chin et al. |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081877 A1 | 4/2010 | Vakharia |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0114033 A1 | 5/2010 | Fischvogt |
| 2010/0130817 A1 | 5/2010 | Conlon |
| 2010/0130821 A1 | 5/2010 | Rosemurgy et al. |
| 2010/0160729 A1 | 6/2010 | Smith et al. |
| 2010/0160735 A1 | 6/2010 | Bakos |
| 2010/0168519 A1 | 7/2010 | Matsuo |
| 2010/0168522 A1 | 7/2010 | Wenchell et al. |

(56) References Cited

U.S. PATENT DOCUMENTS

FOREIGN PATENT DOCUMENTS

| | | |
|---|---|---|
| GB | 2145932 | 4/1985 |
| JP | 2000051361 | 2/2000 |
| JP | 2001009037 | 1/2001 |
| WO | WO 98/50104 A | 11/1998 |
| WO | WO 2004/000410 A | 12/2003 |
| WO | WO 2004/037097 A | 5/2004 |
| WO | WO 2005/023358 A1 | 3/2005 |
| WO | WO 2006/029370 A2 | 3/2006 |
| WO | WO 2007/019117 A | 2/2007 |
| WO | WO 2007/038715 A | 4/2007 |
| WO | WO 2009/140594 A2 | 11/2009 |

OTHER PUBLICATIONS

Article 34 Amendments in PCT/US2009/036173.
Supplemental Letter and Amendments Under Article 34 for PCT/US2009/036173.
International Preliminary Report on Patentability for PCT/US2009/026173 mailed May 7, 2010.
International Search Report/Written Opinion for PCT/US2010/022572 mailed May 21, 2010.
E. Dubcenco, et al., The development of a novel intracolonic occlusion balloon for transcolonic natural orifice transluminal endoscopic surgery: description of the technique and early experience in a porcine model (with Videos); Gastrointestinal Endoscopy, vol. 68, No. 4, 2008, pp. 760-766.
International Search Report/Written Opinion for PCT/US2008/079199 mailed Jan. 22, 2009.
Article 34 Amendments in PCT/US2008/079199.
International Preliminary Report on Patentability for PCT/US2008/079199 mailed Jan. 15, 2010.
International Search Report in PCT/US09/044143 dated Jan. 18, 2011.
International Preliminary Report on Patentability in PCT/US09/044143 issued Jan. 25, 2011.

* cited by examiner

SYSTEMS, DEVICES AND METHODS FOR ACCESSING A BODILY OPENING

CROSS-REFERENCE TO RELATED APPLICATIONS

This application is a continuation-in-part of U.S. application Ser. No. 12/466,866 filed on May 15, 2009, entitled "SYSTEMS, DEVICES AND METHODS FOR ACCESSING A BODILY OPENING" the entire contents of which are incorporated herein by reference.

FIELD OF THE INVENTION

The present invention relates generally to medical systems, devices and methods to access a bodily opening via a bodily lumen, such as an opening in a wall of the gastrointestinal tract, for deployment of an endoscope and/or other medical devices.

BACKGROUND OF THE INVENTION

Openings in bodily walls may be formed to gain access to adjacent structures of the body, such techniques being commonly referred to as translumenal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies, tubal ligations, or other operations, all in a minimally invasive manner. Many translumenal procedures for gaining access to various body cavities using other bodily lumens have also been developed. For example, the bodily lumens of the gastrointestinal tract are often endoscopically explored and can be utilized to provide access to the peritoneal cavity and other body cavities. U.S. patent application Ser. No. 12/025,985 filed Feb. 5, 2008, discloses such a procedure, and is incorporated herein by reference in its entirety.

Although translumenal procedures are minimally invasive, there are also various risks involved. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection. Traditional overtubes have been used to protect the mouth and esophagus while delivering an endoscope to the stomach. However, these overtubes do not seal to the gastric wall. Furthermore, traditional overtubes are quite rigid and can restrict the ability to manipulate the endoscope as desired.

BRIEF SUMMARY OF THE INVENTION

The present invention provides medical systems, devices and methods for accessing a bodily opening that are, among other things, safe and reliable, and that aid in the manipulation of the endoscope of other medical tool. One embodiment of a medical device for forming a pathway from an external orifice to a bodily opening defined by tissue of an internal bodily lumen is provided in accordance with the teachings of the present invention, and generally includes an expandable frame and a flexible sheath. The flexible sheath has a length suitable for forming the pathway and has a distal portion that is collapsible. The expandable frame is connected to the distal portion of the sheath. The expandable frame is operable between a collapsed configuration and an expanded configuration, the expandable frame expanding radially from the collapsed configuration to the expanded configuration. The expandable frame includes a first cage having a proximal segment and a distal segment connected together by intermediate hinges. The proximal segment is connected to the flexible sheath, while the distal segment projects distally beyond the distal portion of the flexible sheath.

According to more detailed aspects, the first cage is defined by a plurality of struts having proximal and distal ends, the struts of the proximal segment connected together at their proximal ends by proximal hinges, the struts of the distal segment connected together at their distal ends by distal hinges. The plurality of struts rotate relative to one another about the proximal and distal hinges to permit the proximal and distal segments of the first cage to expand radially from the collapsed configuration to the expanded configuration. The plurality of struts are preferably bent between their proximal and distal ends to define the intermediate hinges. The distal segment of the first cage is preferably angled about 45 degrees to about 90 degrees relative to the proximal segment of the first cage in the expanded configuration, and most preferably about 75 degrees. Pairs of struts are connected at their distal ends to define arms. In one embodiment, each pair of struts criss-cross proximate the intermediate hinges. Preferably, the first cage and the plurality of struts are formed by a single wire bent into a configuration defining the proximal segment, the distal segment, and the intermediate hinges. The ends of the single wire may be joined together to form a continuous path.

According to still further aspects, the distal ends of the plurality of struts may define a plurality of loops. The medical device may also include a suture extending through the plurality of loops and proximally through the flexible sheath. The suture preferably includes a distal end forming a suture loop located between the plurality of loops, a proximal end of the suture passing through the plurality of loops and through the suture loop and then proximally through the flexible sheath. The medical device may also include an elongate tubular member extending through the flexible sheath, the elongate tubular member slidably receiving the suture. The elongate tubular member preferably has a length greater than the length of the flexible sheath A method for accessing a bodily opening defined by tissue of an internal bodily lumen via an external orifice is also provided in accordance with the teachings of the present invention. The method includes the step of providing a medical device comprising an expandable member and a flexible sheath such as those summarized above and described herein. The distal end of the sheath and a portion of the expandable member are delivered within the perforation while the stent is in its collapsed configuration. The expandable member is operated to its expanded configuration such that the distal end of the sheath is placed in contact with the interior of the perforation formed in the bodily wall, and the distal segment of the first cage rotates radially outwardly relative to the proximal segment. The distal segment of the first cage is located distally beyond the perforation and the bodily wall to assist in maintaining the position of the flexible sheath within the perforation. According to more detailed aspects, to remove the medical device an elongate tubular member is introduced through the flexible sheath to a position where a distal end of the elongate tubular member is positioned distally beyond the distal segment of the first cage. A suture connected to the distal ends of the distal segment is retracted to rotate the distal segment radially inwardly relative to the proximal segment.

DETAILED DESCRIPTION OF THE INVENTION

In the present application, the terms "proximal" and "proximally" refer to a position, direction, or orientation that is generally towards a physician during a medical procedure, while the terms "distal" and "distally" refer to a position, direction, or orientation that is generally away from the physician and towards a target site within a patent's anatomy during a medical procedure. Thus, "proximal" and "distal" portions of a device or bodily region may depend on the point of entry for the procedure (e.g., percutaneously or laparoscopically or endoscopically).

Figure 1:
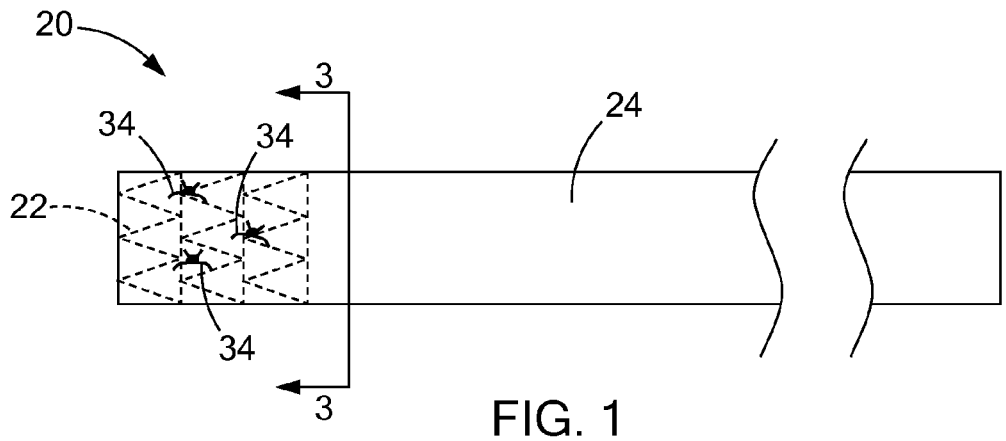
FIG. 1 is a plan view of a medical device constructed in accordance with the teachings of the present invention.
Figure 2:
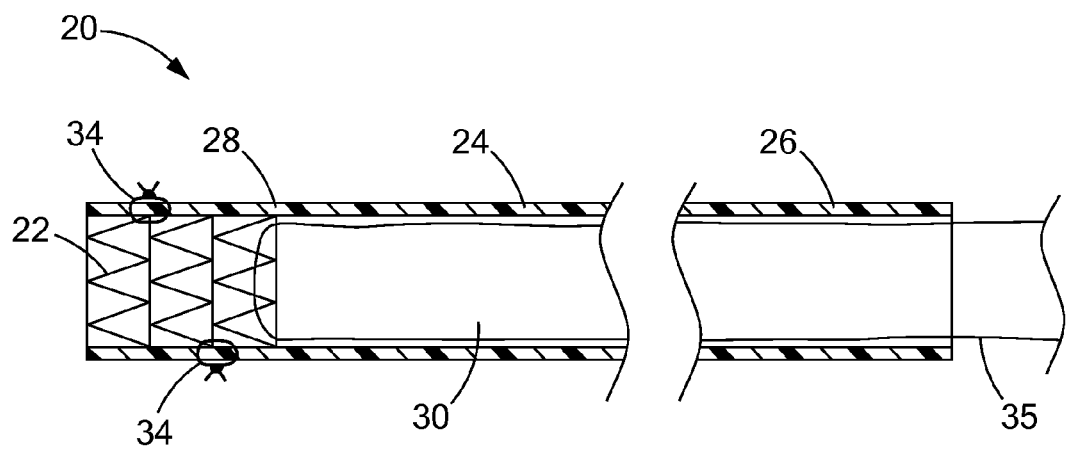
FIG. 2 is a cross-sectional view of the medical device depicted in FIG. 1.
Figure 3:
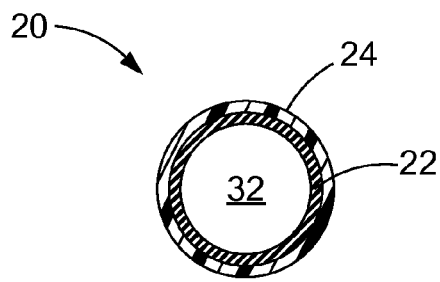
FIG. 3 is a cross-sectional view taken about the line 3-3 in FIG. 1.

Turning now to the figures, FIGS. 1-3 depict a medical device 20 for forming a pathway from an external orifice to a bodily opening defined by tissue of an internal bodily lumen, constructed in accordance with the teachings of the present invention. As is known in the art, the external orifice typically is a natural orifice such as the mouth, anus, vagina, ears, nose, etc., although it will be recognized by those skilled in the art that the medical device 20 may also be employed through intentionally formed orifices such as those made during laparoscopic or similar procedures. Similarly, the bodily opening defined by the tissue of an internal bodily lumen may be intentionally formed or may be naturally occurring, and the internal bodily lumen may comprise a portion of the gastrointestinal tract or any other internal bodily lumen, as will be recognized by those skilled in the art.

The medical device 20 generally comprises an expandable frame 22 and a flexible sheath 24. The flexible sheath 24 generally extends from a proximal portion 26 to a distal portion 28 and has a length suitable for forming the pathway, i.e. its length is sized depending upon the particular orifice and bodily lumen being traversed. The sheath 24 defines a sheath lumen 30 through which an endoscope 100 (FIG. 11) or other medical instrument may be traversed for accessing the bodily opening. Likewise, the expandable frame 22 defines a frame lumen 32 through which the endoscope 100 or other medical instrument may pass.

Figure 4:
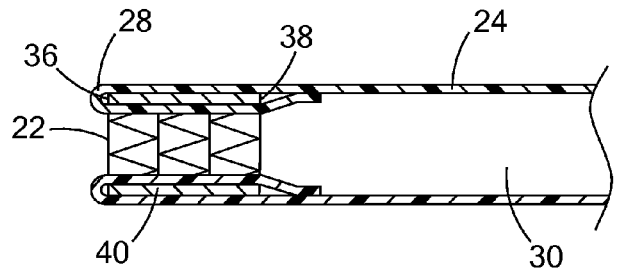
FIG. 4 is a cross-sectional view of another embodiment of the medical device depicted in FIG. 1.

The expandable frame 22 is connected to the distal portion 28 of the sheath 24, and more particularly within the sheath lumen 30 as shown, although the expandable frame 22 may be positioned on the exterior of the sheath 24. In one manner, a plurality of sutures 34 may be threaded through the sheath 24 and the struts 42 of the expandable frame 22, and the ends of the sutures 34 tied to connect the expandable frame 22 and sheath 24 together. In another manner, shown in FIG. 4, the distal portion 28 of the sheath 24 may wrap around a distal end 36 of the expandable frame 22 and extend proximally beyond the proximal end 38 of the expandable frame 22 where it is connected to the sheath 24 using conventional methods such as heat bonding, mechanical bonding, adhesives, fasteners, suturing or the like. As such, the distal portion 28 of the sheath 24 can form a pocket 40 sized to receive the expandable frame 22 and encapsulate it therein.

Figure 5:
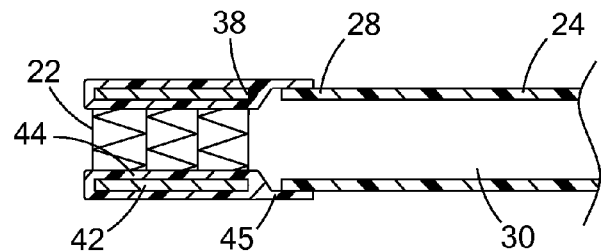
FIG. 5 is a cross-sectional view of another embodiment of the medical device depicted in FIG. 1.

In yet another manner depicted in FIG. 5, the expandable frame 22 and its struts 42 may have a coating 44 (e.g. a polymeric coating) that is formed to extend beyond a proximal end 38 of the expandable frame 22 to define a lip 45. In this configuration, the distal portion 28 of the sheath 24 may be attached to the lip 45 (or any other portion of the coating 44) via conventional methods such as those mentioned above. The coating 44 may define a continuous outer layer, e.g. formed from a separate tubular sheet (of similar or dissimilar materials as the sheath 24), or may be applied to the individual struts 42 to leave spaces therebetween (e.g. in a dip coating process), and thus the surface of the lip 45 may be continuous or discontinuous.

Figure 15:
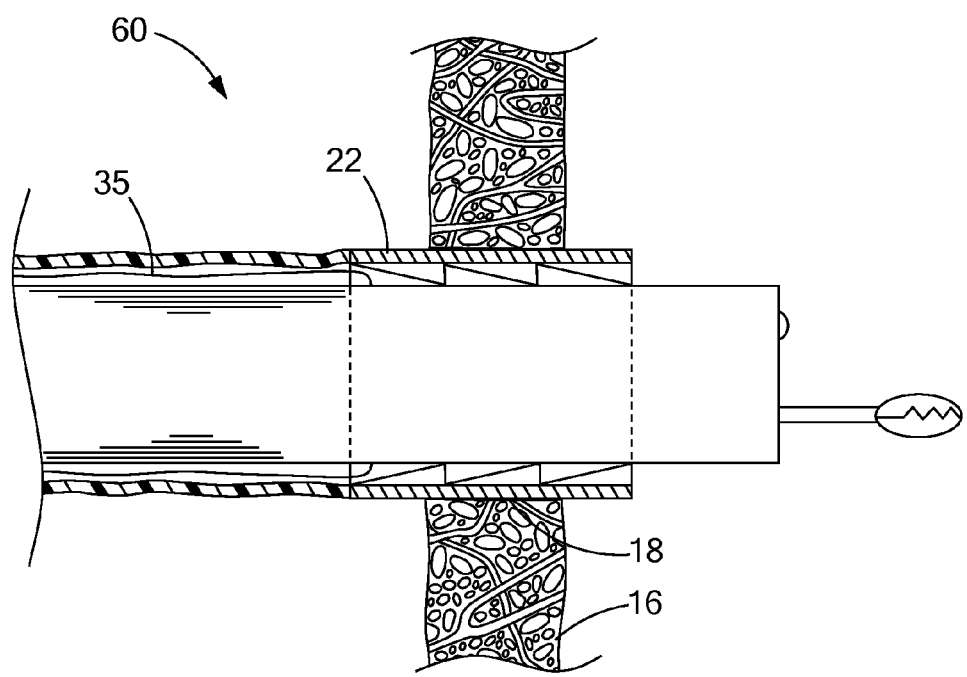
Figure 16:
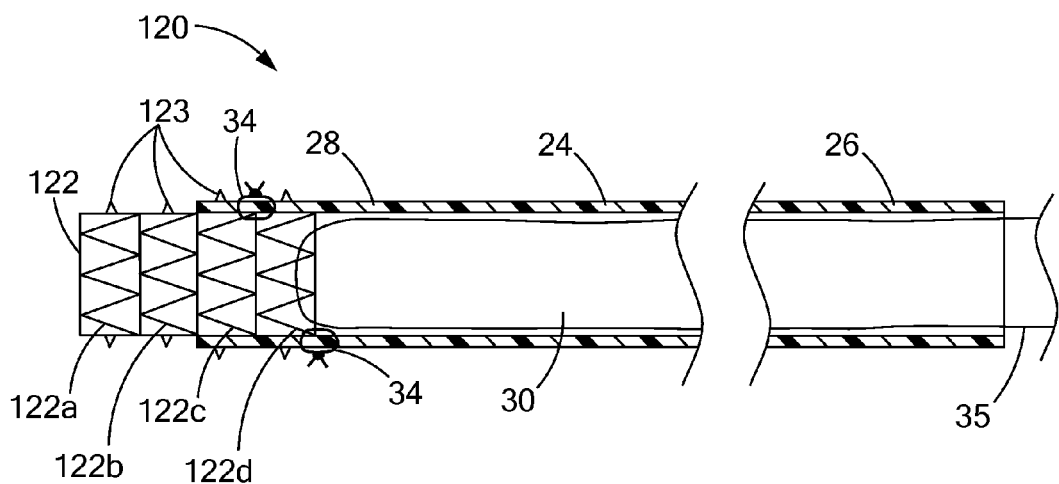
FIG. 16 is a cross-sectional view, similar to FIG. 2, depicting another embodiment of a medical device constructed in accordance with the teachings of the present invention.

In still yet another manner depicted in FIG. 16, the medical device 120 includes an expandable frame 122 having four cages 122a, 122b, 122c, 122d, only two of which (122c, 122d) are covered by the flexible sheath 24. The two distal cages 122a, 122b are exposed on their exterior to directly engage the tissue of the gastric wall 16 within the opening 18 (see, e.g. FIG. 15), thereby improving the friction and grip of the frame 122 to the wall 16. The covered portion of the expandable frame 122 (in the depicted embodiment cages 122c, 122d) may also press the sheath 24 into engagement with the wall 16, although in design and/or use only the uncovered portion of the expandable frame 122 may contact the wall 16. All of the cages in the frame may also be exposed (completely or partially) by attaching the distal end of the sheath to the proximal end of the frame (see, e.g., FIG. 15).

Either or both of the covered and uncovered portions of the expandable frame 122 may also include small barbs 123 which further assist in engaging and gripping the tissue of the wall 16. The barbs 123 project from cages and preferably include sharp edges or points. The barbs 123 may be formed of wire, metal or plastics, and may integrally formed by the material of the frame 122 or separately formed. The barbs 123 may also be formed by removal of material to improve the friction of the exterior of the frame 122, for example a roughened surface. Both large voids and micro sized voids can be formed. Similarly, the distal portion of the sheath 24 itself can also include barbs or roughed materials/surfaces, integrally or separately formed, to improve friction, gripping and retention of the device 20. Further variations in view of the foregoing embodiments will be recognized by the skilled artisan.

Figure 6A:
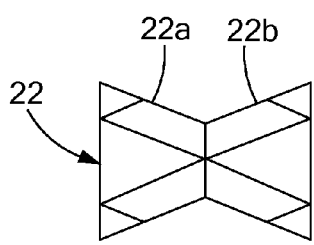
FIGS. 6A, 6B and 6C are plan views of alternate embodiments of expandable frames that may for a portion of the medical devices depicted in FIGS. 1-5.
Figure 6B:
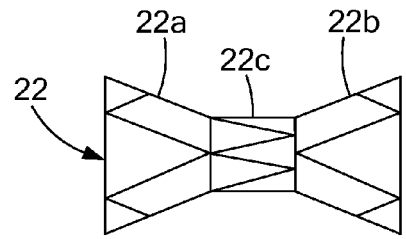
Figure 6C:
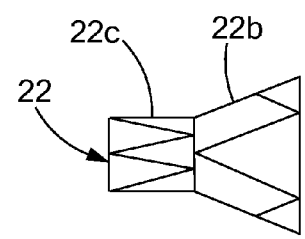

It will be recognized that the expandable frame 22 may take many forms and constructions. The expandable frame 22 is preferably an expandable stent, and most preferably a self-expanding stent such as the zig-zag wire metal stents of the Gianturco type as described in U.S. Pat. No. 4,580,568, the disclosure of which is incorporated by reference herein in its entirety. The expandable frame 22 may also be a balloon expandable stent. The expandable frame 22 may have numerous types of geometries, such as coil designs, open cell designs, multi-cell closed-cell designs, and woven designs. The geometric shapes of the expandable frame 22 may also be of various constructions such as cylindrical (FIG. 2), butterfly shape (e.g. made by two tapering cages 22a, 22b connected together as shown in FIG. 6A), or bow-tie shape (e.g. two tapering cages 22a and 22b interconnected by a cylindrical cage 22c as shown in FIG. 6B), or a flared shape (e.g. a first cylindrical cage 22 having a second tapering cage 22c at its proximal or distal end as shown in FIG. 6C), to name a few. An outer or inner sheath, coating, sutures, bonding or welding techniques may be used to connect multiple cages, as is known in the art. The frame 22 and its expandable struts 42 are preferably formed of a material having a rigidity greater than the sheath 24, e.g. a metal or alloy such as nitinol, or plastics having sufficient rigidity and flexure strength.

Figure 7:
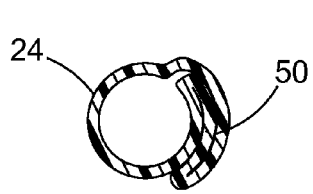
FIG. 7 is a cross-sectional view showing one embodiment of the collapsed configuration of the medical device depicted in FIG. 1.
Figure 8:
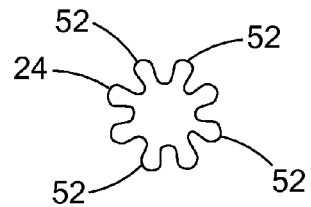
FIG. 8 is a cross-section view of another embodiment of a collapsed configuration of the medical device depicted in FIG. 1.

The expandable frame 22 is generally operable between a collapsed configuration (see e.g., FIGS. 9 and 10) and an expanded configuration (see e.g., FIGS. 1-3 and 13 and 14). Similarly, the sheath 24 is operable between a collapsed configuration (see, e.g., FIGS. 7 and 8), and an expanded configuration (see, e.g., FIGS. 1-3 and 13 and 14). The flexible sheath 24 is preferably formed of a flexible material such as a polymer so that it is collapsible over a substantial portion of its length. That is, the sheath 24 should be collapsible over at least the portion that is intended to be located within the body, which will include the distal portion and generally be at least half the overall length of the sheath 24. Accordingly, the sheath 24 preferably has a rigidity less than traditional overtubes and trocar sleeves. Generally, the sheath 24 folds onto itself in the collapsed configuration. As shown in FIG. 7, one collapsed configuration of the sheath 24 may include one or more large folds 50 which reduces the outer diameter of the sheath 24. As shown in FIG. 8, the sheath 24 may include a series of smaller folds 52, such as folding the sheath 24 in an accordion-style, to reduce its outer diameter in the collapsed configuration.

The flexible nature and collapsibility of the sheath 24 should be designed not only so that it may take a collapsed configuration such as those depicted, but also so that it does not restrict operability of an endoscope or other medical instrument passed through the sheath lumen 30. This can be controlled through selection of the plastic material, e.g. based on its durometer and thickness. Preferably, the sheath 24 has a thickness in the range of about 0.001 inches to about 0.1 inches, and has a sheet-like quality (in-fact, a sheet may be rolled and its edges connected to form the sheath 24). Suitable materials include fluoroplastics such as polytetrafluorethylene (PTFE) or Teflon™, polyethylenes (high, medium or low density), polyethylene ether ketones (PEEK), polyurethanes, silicones or polyamides such as Nylon™. Most preferably, the sheath 24 is formed of low density polyurethane. The structure of the flexible sheath 24 can include multi-layer or single layer constructions with or without reinforcement wires, coils or filaments. Likewise, a polyvinylchloride (PVC) coating may also be employed for increased durability, without making the sheath 24 too rigid.

By utilizing a flexible polymer or elastomer, manipulation and operation of the endoscope 100 or other medical instrument is not compromised. Accordingly, not only can the medical device 20 facilitate operation of the medical instrument, but navigation deeper within the gastrointestinal tract via a natural bodily opening is possible. At the same time, the medical device 20 is easy to deploy and provides a secure engagement and fluidic seal with the internal bodily opening in the tissue that can prevent unwanted travel of bacteria laden fluids. Preferably, the sheath 24 has a diameter about equal to or greater than an estimated diameter of the bodily lumen (such as the esophagus 12), and collapses under a radial force that is less than the radial force anticipated from the bodily lumen. In such a configuration, the sheath 24 will not itself cause dilation or expansion of the esophagus 12 or other bodily lumen.

Figure 9:
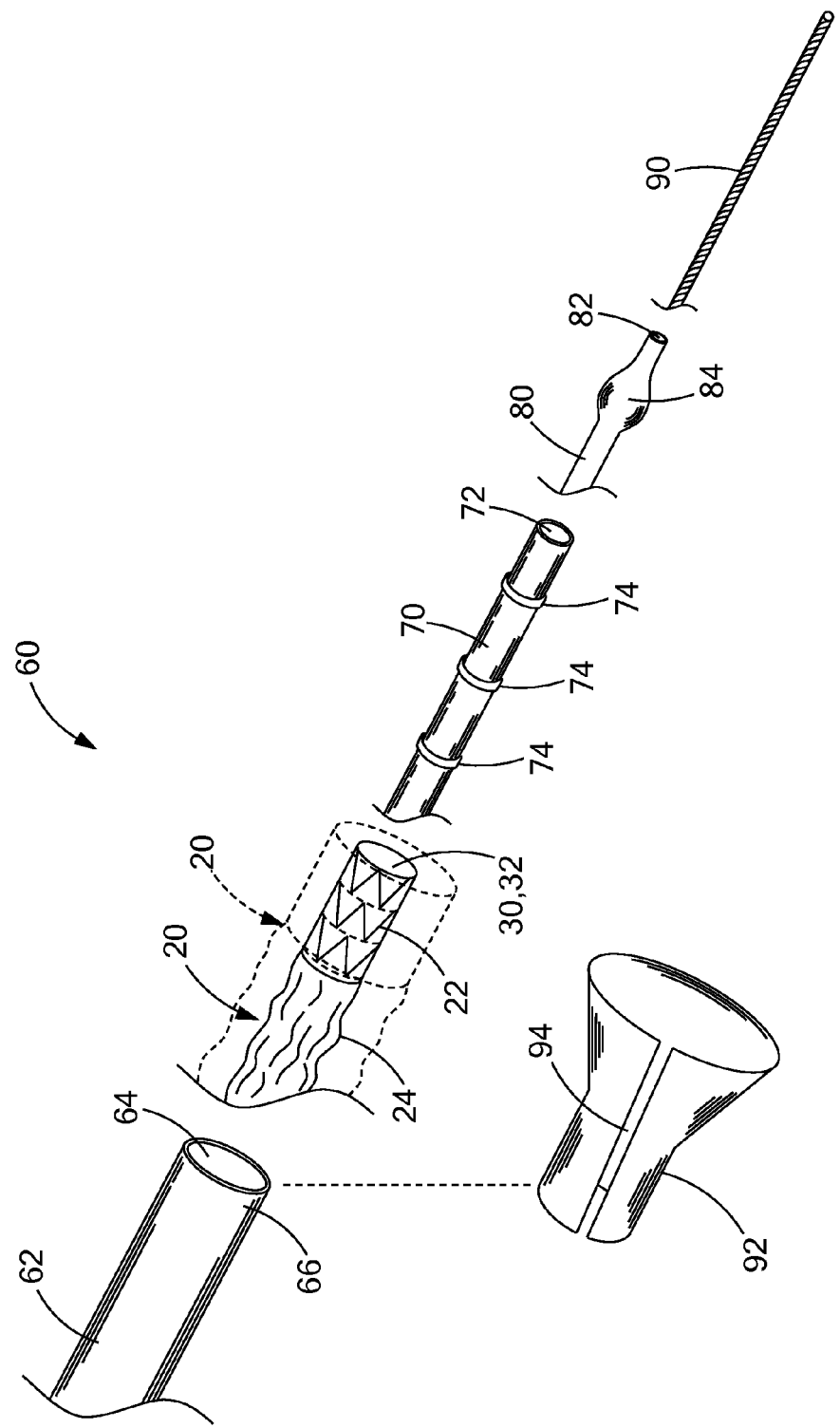
FIG. 9 is an exploded view of a medical system for deploying the medical device depicted in FIGS. 1-5, constructed in accordance with the teachings of the present invention.
Figure 10:
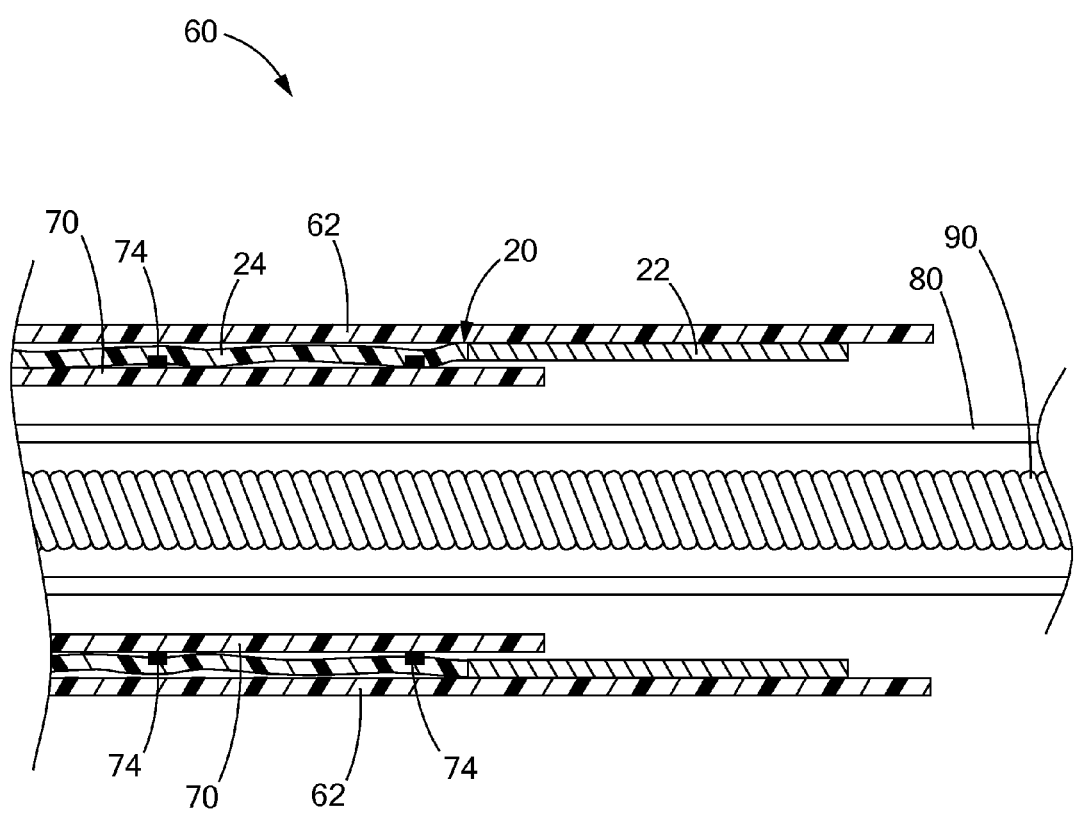
FIG. 10 is a cross-sectional view of the medical system depicted in FIG. 9.

Turning now to FIGS. 9 and 10, a medical system 60 for forming the pathway from an external orifice to a bodily opening is provided in accordance with the teachings of the present invention. The medical system 60 generally includes a medical device 20, such as those previously described, although it will be recognized that the medical system 60 may also be used with other medical devices 20 having an elongated sheath and a radially expandable member attached to a distal end of the sheath. The medical system 60 includes an outer catheter 62 defining an outer catheter lumen 64 sized to receive the medical device 20 in its collapsed configuration (shown in solid lines in FIG. 9). An inner catheter 70 is sized to be received within the sheath lumen 30 and stent lumen 32. The inner catheter 70 defines an inner catheter lumen 72. A plurality of gripping members 74 are positioned on the exterior of the inner catheter 70 and are longitudinally spaced apart. Preferably, the gripping members 74 each comprise an O-ring, gasket or other elastomeric member that may be fitted on the exterior of the inner catheter 70 by way of adhesives, bonding or simple friction fit. The gripping members 74 may have a circular cross-sectional shape, or non-circular cross-sectional shapes such as square, rectangular, triangular, oval or oblong, etc. As will be discussed in further detail herein, the gripping members 74 serve to grasp the medical device 20, and in particular the flexible sheath 24, and hold it in place while the outer catheter 62 is retracted to deploy the stent 22 and medical device 20.

The medical system 60 may optionally include a guiding catheter 80 which defines a guiding lumen 82 sized to receive a wire guide 90. The guiding catheter 80 may include a bulb-shaped distal end 84 that assists with loading and deploying the medical system 60, and delivering the same over the wire guide 90 to the bodily opening. Also shown in FIG. 9 is a funnel 92 having a slot 94 which is used for loading the medical system 60 (the loaded state is shown in FIG. 10), as will now be described. Generally, the guiding catheter 80 is loaded within the inner catheter lumen 72 of the inner catheter 70. In turn, the inner catheter 70 and guiding catheter 80 are loaded within the lumens 30, 32 of the medical device 20 in its expanded configuration (shown in dotted lines in FIG. 9). The funnel 92 is attached to a distal end 66 of the outer catheter 62 and the proximal end of the medical device 20 (namely proximal portion 26 of sheath 24) and inner catheter 70 and guiding catheter 80 may be moved through the outer catheter lumen 64 towards its proximal end. Due to the flexible and collapsible nature of the sheath 24, it will naturally take its collapsed configuration as it is positioned within the outer catheter lumen 64, although the sheath may be manually folded or otherwise manipulated as it is loaded within the outer catheter 62 to have any preferred collapsed configuration. The outer catheter 62 will be shorter than the medical device 20, inner catheter 70 and guiding catheter 80, so that their proximal ends may be grasped and pulled proximally. This causes the stent 22 of the medical device 20 to pass through the funnel 92, causing it to take its collapsed configuration and be received within the outer catheter lumen 64 of the outer catheter 62. Once the medical device 20 and inner catheter 70 (and optionally guiding catheter 80) are loaded within the outer catheter 62, such as is shown in FIG. 10, the funnel 92 may be removed from the outer catheter 62.

Figure 11:
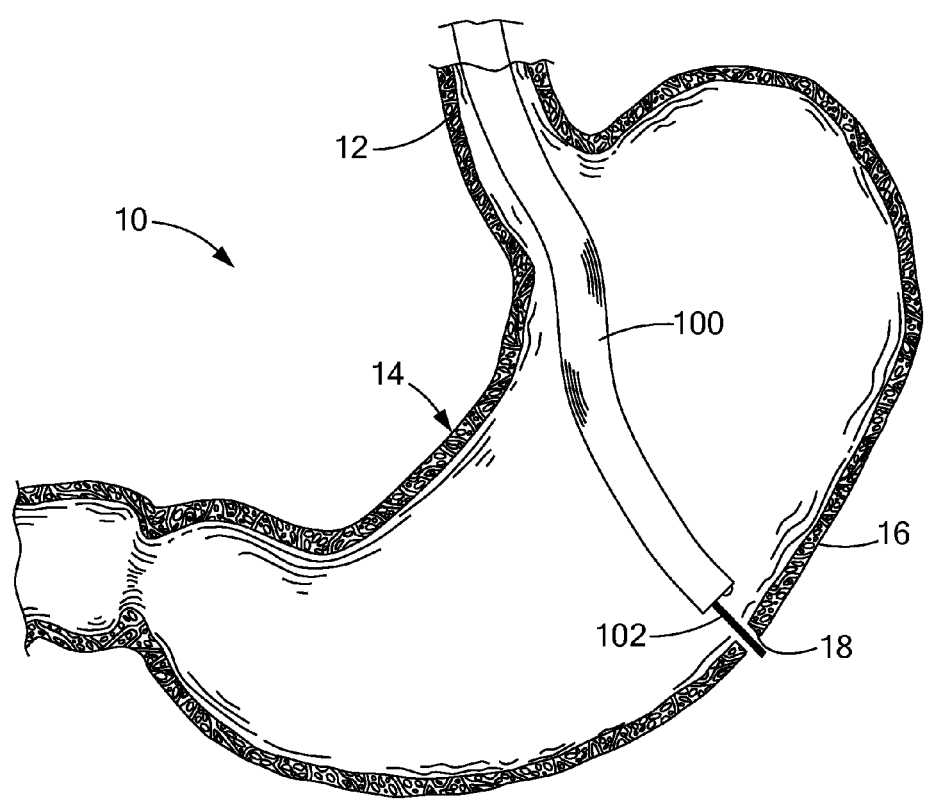
FIGS. 11-15 depict a method of employing the medical systems and devices depicted in FIGS. 1-10.
Figure 12:
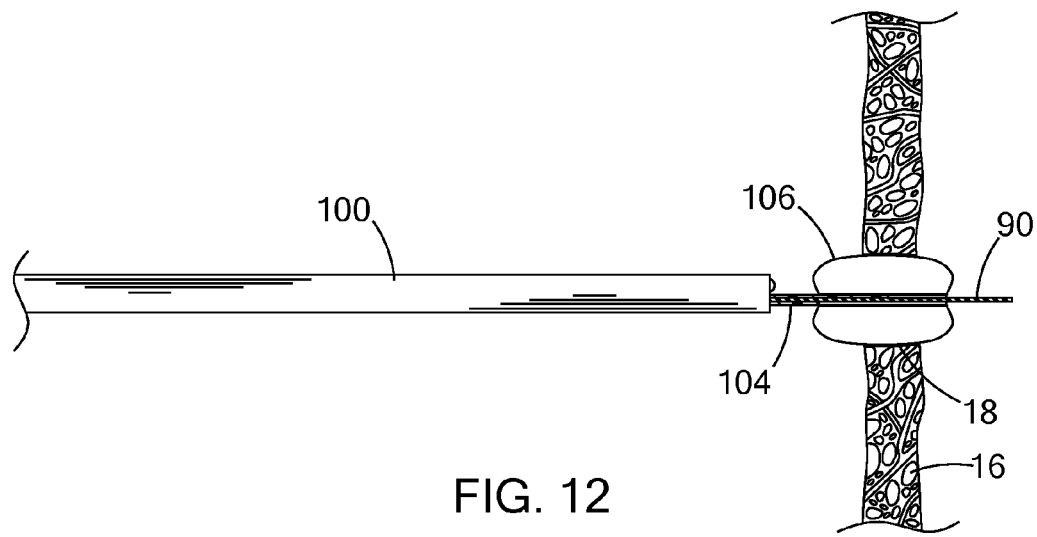

One preferred method for utilizing the medical system 60 and deploying the medical device 20 will now be described with reference to FIGS. 11-15. As shown in FIG. 11, an upper portion of the gastrointestinal tract 10, such as the esophagus 12 and stomach 14, may be accessed via the mouth (not shown). An endoscope 100 may be introduced into the stomach 14, and a cutting instrument 102 may be employed through a working channel of the endoscope 100 to form an opening 18 in the gastric tissue or gastric wall 16. As shown in FIG. 12, the wire guide 90 may be placed through the opening 18, and a dilator 104 may be introduced over the wire guide 90. Generally, the dilator 104 may include an inflation balloon 106 or other radially expandable member to enlarge the opening 18 formed in the gastric wall 16.

Figure 13:
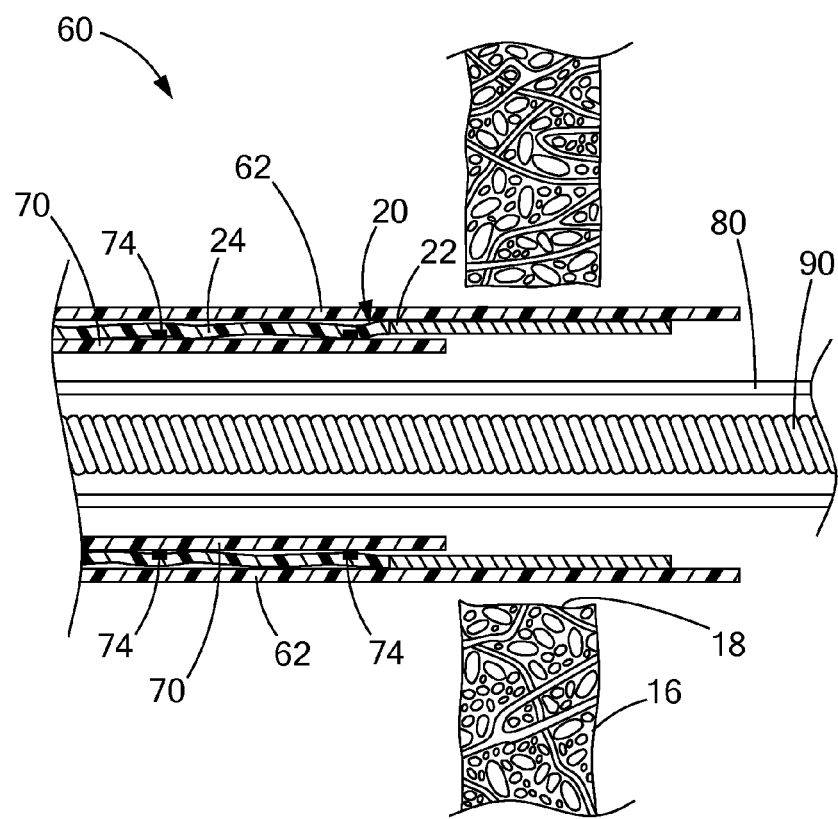

As shown in FIG. 13, the endoscope 100 and dilator 104 may be removed while leaving the wire guide 90 in place, and the medical system 60 advanced distally over the wire guide 90 to a position proximate the opening 18. More particularly, the medical system 60 is preferably positioned such that a portion of the expandable frame 22 of the medical device 20 is positioned within the opening 18. To accomplish this, fluoroscopic or ultrasonic monitoring techniques may be employed, whereby the expandable frame 22 may serve as the viewable element, although the outer catheter 62, the distal portion 28 of the sheath 24, or even the inner catheter 70, may include markings such as radiopaque bands or the like that facilitate visualization. Similarly, a catheter-based fiber-optic visualization system or a smaller endoscope (such as a pediatric endoscope), may be placed through the mouth and esophagus 12 into the stomach 14 (parallel to the medical system 60) for direct visualization of the medical system 60.

Figure 14:
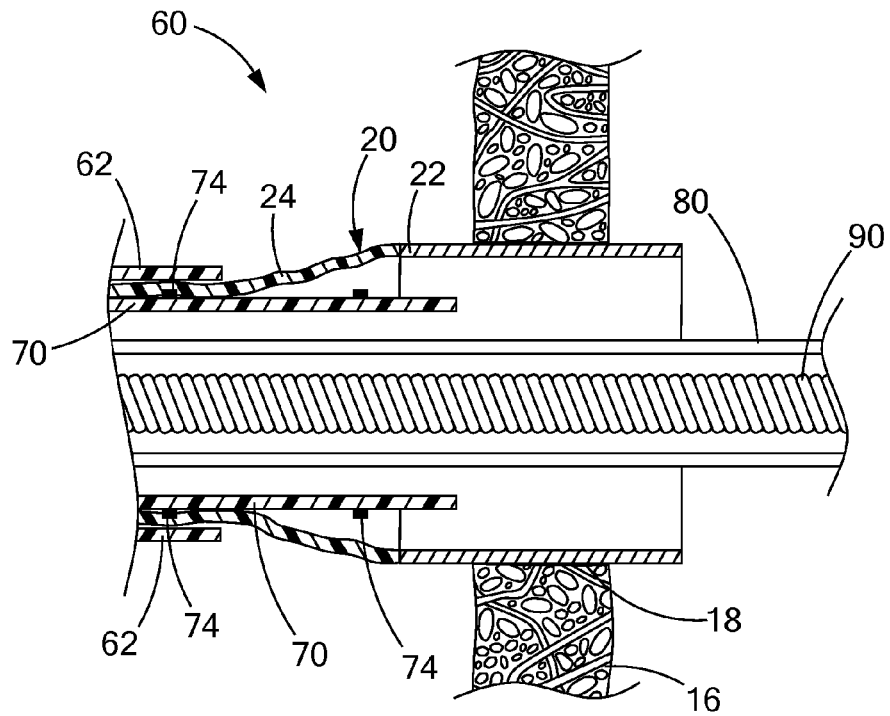

As shown in FIG. 14, the outer catheter 62 is retracted proximally relative to the inner catheter 70, which is preferably held in place. The gripping members 74 of the outer catheter 70 serve to engage the medical device 20, and in particular the sheath 24, to maintain its position and prevent it from sliding or folding or kinking due to its flexible nature, while the outer catheter 62 is retracted. As the expandable frame 22 becomes exposed beyond the distal end 66 of the outer catheter 62, it will take its expanded configuration and press against the tissue 16 defining the opening 18. Through appropriate sizing of the expandable frame 22, the medical device 20 will be firmly affixed to the gastric wall 16 and within the opening 18, thereby forming a port and passageway from the mouth to the bodily opening 18. The expandable frame 22 exerts a radially outward force on the flexible sheath 24 and the gastric wall tissue 16 sufficient to open and hold-open the opening 18, as well as affix the flexible sheath 24 and medical device 20 to the gastric wall 16. Visualization of the sutures 34 holding the expandable frame 22 and sheath 24 together can assist in confirming complete deployment of the expandable frame 22.

With the medical device 20 in place, the outer catheter 62 and inner catheter 70 and guiding catheter 80 may be retracted proximally and disposed of. Then, the endoscope 100 or a new endoscope may be advanced distally through the flexible sheath 24 of the medical device 20 and through the opening 18 formed in the gastric wall 16 for performing a translumenal procedure. It will be recognized by those skilled in the art that many other medical devices, in addition to or in conjunction with, an endoscope may be employed through the passageway of the medical device 20. When it is desired to remove the medical device 24, the suture 35 (see FIGS. 2 and 15) may be pulled proximally to collapse the cages of the expandable frame 22, allowing the expandable frame 22 and device 20 to be removed from the opening 18 in the gastric wall 16.

Figure 17:
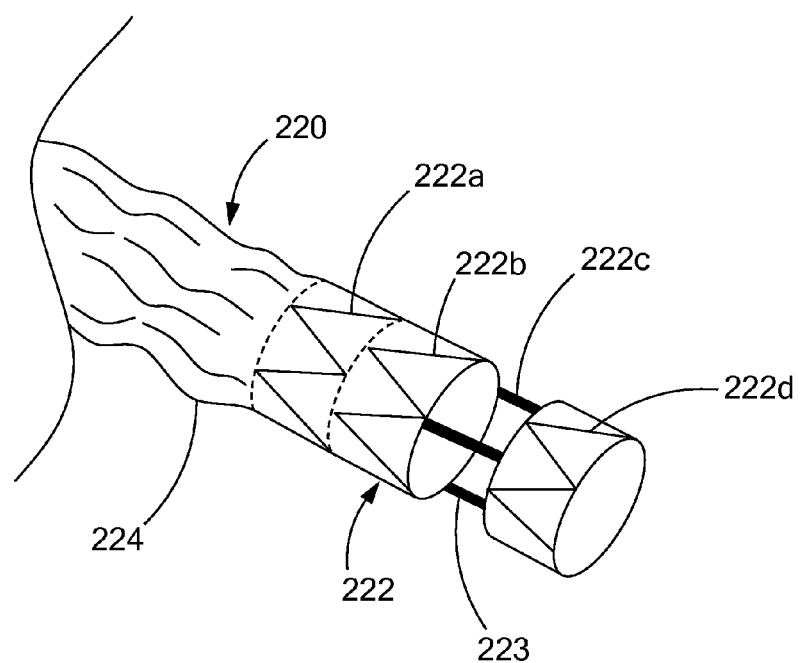
FIG. 17 is a perspective view and FIG. 18 is a cross-sectional view depicting yet another embodiment of a medical device constructed in accordance with the teachings of the present invention.
Figure 18:
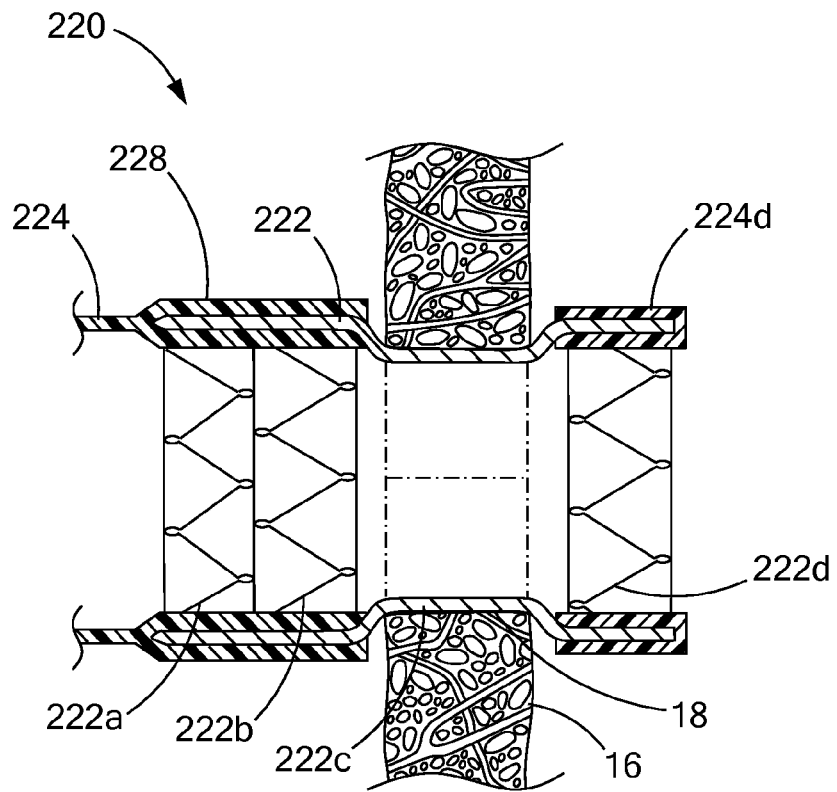

Another embodiment a medical device 220, constructed in accordance with the teachings of the present invention, is shown in FIGS. 17-18. Similar to prior embodiments, the device 220 includes an expandable frame 222 connected to a flexible sheath 224, such as those described above. In this embodiment, the expandable frame 222 includes four cages 222a, 222b, 222c, 222d. The first, second and fourth cages 222a, 222b, 222d are formed as stents, e.g. from zig-zag shaped struts as described above. The third cage 222c is simply formed from two or more strands 223, three strands being shown in FIGS. 18-19. The strands 223 extend longitudinally between the second and fourth cages 222b, 222d to connect these cages while spacing them apart. The strands 223 may extend linearly or be curved, and may be formed from metal wires, plastic strips or the like. Cages 222a, 222b, 222d have been shown as encapsulated by the sheath 224, and the third cage includes a separate coating 224d, although the cages 222a, 222b, 222d may be left exposed as described above. As such, the strands 223 may connect to either the struts of the cages 222b, 222d, or to the sheath/coating 224, 224d.

As best seen in FIG. 18, the strands 223 are exposed to directly engage the tissue of the gastric wall 16 within the opening 18. By virtue of the other cages 222a, 222b, 222d expanding while the natural elasticity of the wall 16 tends to close the opening 18, the strands 223 of the cage 222c are pressed into the wall 16 to firmly secure the medical device 220. The strands 223 are constructed with some flexibility and natural resiliency, and thus the other cages 222a, 222b, 222d tend to have a larger diameter than the opening 18 in their expanded configuration. Preferably the strands 223 extend longitudinally a distance greater than a thickness of the gastric wall 16. At the same time, due to the large spaces between the strands 223, the tissue of the gastric wall 16 tends to extend through the exterior of the cage 222c and into the interior space of the expandable frame 222. Due to the natural elasticity of the wall 16, the tissue may extend inwardly until the tissue edges 17 (defining the opening 18 in the wall 16)

contact each other. As such, the tissue of the wall 16 thus defines a valve that restricts the flow of fluids and the like through the interior of the expandable frame 222 and sheath 224. When an elongate medical device, such as an endoscope, is moved distally through the sheath 224 and frame 222, the device will separate the tissue as it extends distally beyond the wall 16 and device 220, and can similarly seal to the edges 17 in the area of the third cage 222c.

Figure 19:
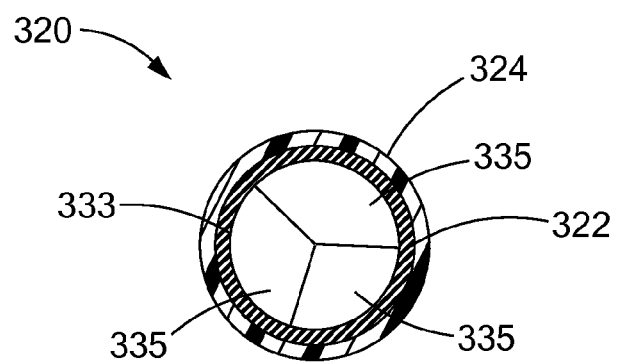
FIG. 19 is a cross-section view, similar to FIG. 3, depicting a variation of the embodiments of the medical devices constructed in accordance with the teachings of the present invention.

Similarly, it will also be recognized by those skilled in the art that in any of the embodiments, a separate valve member may be employed within the interior of the device 20, 120, 220, preferably at its distal end. For example, as shown in FIG. 19, a flap valve 333 may extend within the opening 332 of the expandable frame 322 and sheath 324, and the flap valve may have one or more flexible flaps 335 that contact each other and the interior wall of the device 320. The flaps 335, three being shown in FIG. 19, bend or rotate in response to sufficient longitudinal force (e.g. from an endoscope but not from fluid pressure), and therefore serve as a seal to restrict the movement of fluids and the like through the device 320.

Figure 20:
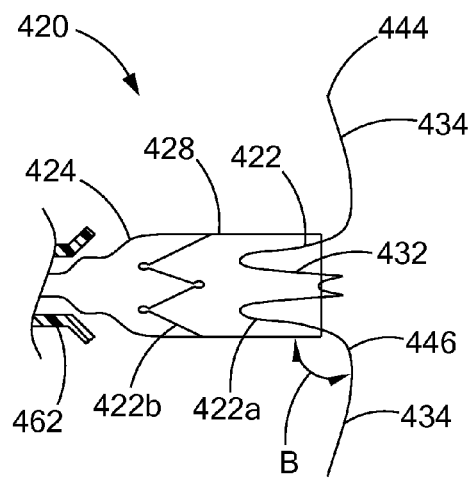
FIG. 20 is a side view depicting yet another embodiment of a medical device constructed in accordance with the teachings of the present invention.
Figure 21:
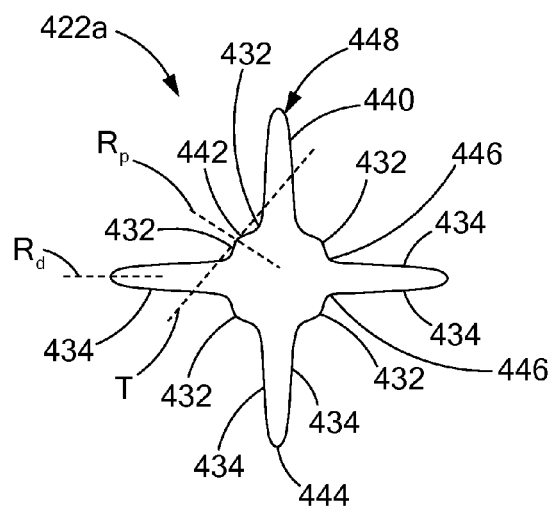
FIG. 21 is a front view of a first cage forming a portion of the medical device depicted in FIG. 20.
Figure 22:
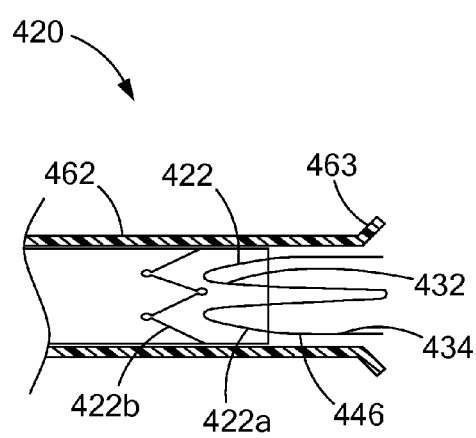
FIG. 22 is a side view of the medical device of FIG. 20 shown in a collapsed configuration.

Another embodiment a medical device 420, constructed in accordance with the teachings of the present invention, is shown in FIGS. 20-22. Similar to prior embodiments, the device 420 includes an expandable frame 422 connected to a flexible sheath 424, such as those described above. As with the prior embodiments, the expandable frame 422 has a length substantially shorter than the flexible sheath 424, and is connected only to a distal portion 428 of the sheath 424. In this embodiment, the expandable frame 422 includes two cages 422a and 422b. The first cage 422a is located distally to the second cage 422b. The second cage 422b, is formed as a cylindrical stent, e.g. from zig-zag shaped struts as described above. The first cage 422a in this embodiment is uniquely formed by a proximal segment 432 and a distal segment 434.

The proximal segment 432 of the first cage 422a is generally positioned within and connected to the flexible sheath 424. The distal segment 434 projects distally beyond the distal portion 428 of the flexible sheath 424. Notably, the proximal segment 432 and distal segment 434 are connected together by intermediate hinges 446. The intermediate hinges 446 permit the distal segment to rotate radially outwardly relative to the proximal segment 432 when the expandable frame 422 expands radially from the collapsed configuration to the expanded configuration. In FIG. 20 the expandable frame 422, including the first cage 422a, is shown in the expanded configuration, while FIG. 22 shows the expandable frame 422 and its first cage 422a in the collapsed configuration.

Preferably, in the expanded configuration the distal segment 434 is rotated relative to the proximal segment an angle β that is about 45° to about 90°, and preferably about 75°. It will be recognized that by utilizing a first cage 422a having a distal segment 434 projecting beyond the distal portion 428 of the flexible sheath 424, and further permitting the distal segment 434 to rotate radially outwardly relative to the proximal segment 432, the distal segment 434 can wrap around and engage the tissue 16 to facilitate engagement of the sheath 424 to the opening 18 in the tissue 16 (see FIGS. 24 and 26 discussed later herein).

As best seen in FIGS. 20 and 21, the first cage 422a is formed by a plurality of struts, which in the depicted embodiment is formed by a single wire strand 440. That is, the wire strand 440 is bent or otherwise formed into a configuration defining the struts of the proximal segment 432, the distal segment 434 and the hinges. Preferably, the ends of the single wire strand 440 are joined together to form a continuous path, as best seen in FIG. 21. The path thus alternates between the proximal segment 432 and the distal segment 434. In particular, the adjacent struts of the proximal segment 432 are connected at their proximal ends to define proximal hinges 442. Similarly, the adjacent struts of the distal segment 434 are connected at their distal ends to define distal hinges 444. Pair of adjacent struts of the distal segment 434 form rotating arms 448 which extend through the opening 16 and retroflex to engage the tissue 16.

Generally, the proximal hinges 442 and the distal hinges 444 permit radial expansion of the expandable frame 422, while the intermediate hinge 446 permits the distal segment 434 to rotate relative to the proximal segment 432. As shown in FIG. 21, the distal hinges 444 permit rotation between adjacent struts relative to a radial axis $R_d$, and the proximal hinges 442 permit rotation between adjacent struts relative to a radial axis $R_p$. At the same time, the intermediate hinges 446 permit relative rotation between the proximal segment 432 and the distal segment 434 relative to a tangential axis T. As shown in FIG. 22, the sheath 424 and expandable frame 422 may be translated relative to a delivery catheter 462 having a flared distal end 463 that permits the frame 422 and sheath 424 to take their collapsed configurations within the delivery catheter 462.

Figure 23:
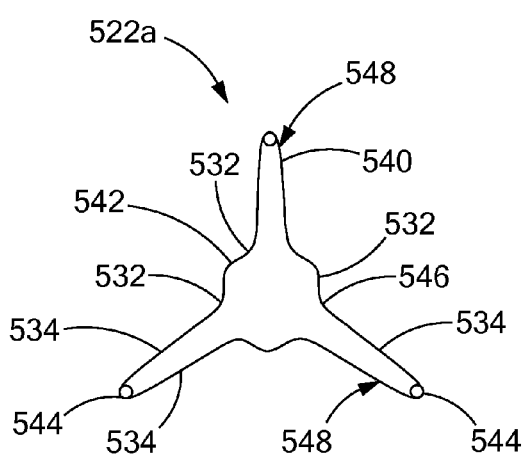
FIG. 23 is a front view of an alternate embodiment of the first cage depicted in FIG. 21.

Another embodiment of a first cage 522a, constructed in accordance with the teachings of the present invention, is shown in FIG. 23. Similar to the embodiment of FIGS. 20-22, the first cage 522a includes a proximal segment 532 and a distal segment 534 interconnected by an intermediate hinge 546. As with the prior embodiment, the plurality of struts defining the first cage 522a are formed from a single wire strand 540 that is bent into a configuration defining the proximal segment 532, distal segment 534 and the hinges. In particular, the adjacent struts of the proximal segment 532 are connected to form proximal hinges 542, while the adjacent struts of the distal segment 534 are connected to form distal hinges 544 and arms 548. However, in this embodiment the distal hinges 544 are formed by coiling the wire strand 540 through at least one complete turn to form a loop therethrough. The proximal hinges 542 could also be formed in a similar manner to define loops. It will also be noted that in the embodiment of FIG. 23, adjacent pairs of struts of the distal segment 534 define three arms 548, whereas four arms 448 are depicted in the embodiment of FIGS. 20-22.

Figure 24:
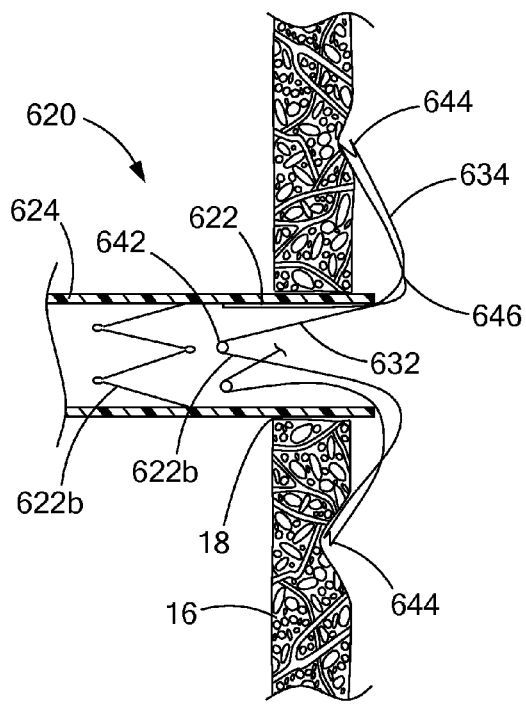
FIG. 24 is a side view, partly in cross-section, illustrating another alternate embodiment of a medical device constructed in accordance with the teachings of the present invention.
Figure 25:
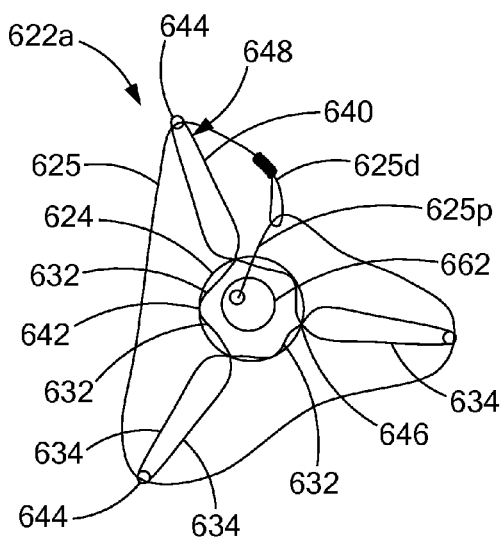
FIG. 25 is a front view of the medical device depicted in FIG. 24.
Figure 26:
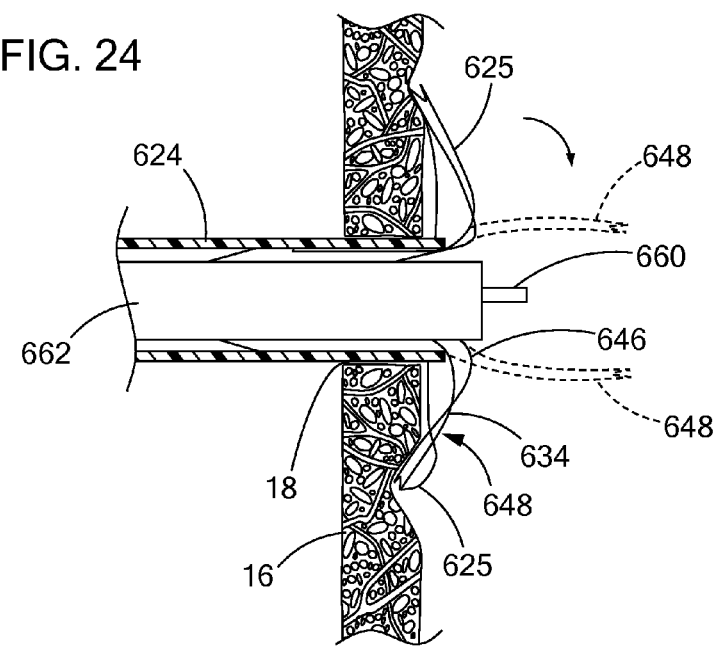
FIG. 26 is a side view of the medical device depicted in FIG. 24.

Yet another embodiment of a medical device 620, constructed in accordance with the teachings of the present invention, is shown in FIGS. 24-26. Similar to the embodiments of FIGS. 20-22 and 23, the device 620 includes an expandable frame 622 connected to a distal portion 628 of a flexible sheath 624, such as those described above. In this embodiment, the expandable frame 622 includes two cages 622a and 622b. The second cage 622b is located proximally to the first cage 622a, and the second cage 622b is formed as a cylindrical stent such as those described above. In FIG. 24, the medical device 620 has been shown in its expanded configuration and positioned within a perforation 18 formed in the tissue 16.

Notably, the cage 622a includes a proximal segment 632 and a distal segment 634 interconnected by an intermediate hinge 646. The first cage 622a is formed by a plurality of struts, and more particularly a single wire strand 640 bent into a configuration defining the proximal segment 632, distal segment 634 and the hinges. In particular, the struts of the proximal segment 632 are connected at their proximal ends to form proximal hinges 642, and the struts of the distal segment are connected at their distal ends to define distal hinges 644. In this embodiment, the distal hinges 644 are again formed by a coil in the wire strand 640 to define a loop. An intermediate hinge 646 connects the distal segment 634 and the proximal segment 632, and provides for relative rotation therebetween. The intermediate hinge 646 is formed by a bend in the wire strand 640 located between the two segments 632, 634.

As best seen in FIG. 25, the single wire strand 640 is again bent into a shape to form a continuous path. The path alternates between a pair of struts forming part of the proximal segment 632, to a pair of struts forming an arm 648 of the distal segment 634. This configuration is repeated to form three arms 648 of the distal segment 634. Notably, the struts of the wire strand 640 criss-cross at a location proximate the intermediate hinge 646. This facilitates forming the coiled loop at the distal hinges 644 with a minimal length of the wire strand 640, while also facilitating the formation of the intermediate hinge 646 at a desired point.

It can also be seen in FIGS. 25 and 26 that a suture 625 has been strung through the loops of the distal hinges 644. In particular, a distal portion 625d of the suture 625 has been formed into a suture loop, and the proximal portion 625p of the suture 625 has been strung through each of the loops of the distal hinges 644 and then through the suture loop at the suture's distal end 625d. The proximal portion 625p of the suture 625 then extends proximally through the flexible sheath 624. Preferably, the proximal portion 625p of the suture 625 extends through a elongated tubular member such as catheter 660, which is shown extending through the working channel of an endoscope 662 in FIG. 26.

In order to collapse the distal segment 634 of the first cage 622a, and in particular the three arms 648, the catheter 660 is positioned distally beyond the distal segment 634, and in particular beyond the intermediate hinges 646. This creates a distally directed force on the arms 648 to pull the arms 648 radially inwardly (and distally forward) as shown by the dotted lines in FIG. 26. In this manner, the medical device 620, including the flexible sheath 624 and expandable frame 622, may be removed from the patient. The catheter 660 or other elongate tubular member thus has a length greater than the length of the flexible sheath 624.

In view of the foregoing description of various embodiments of the medical devices, systems and methods, it will be recognized that by utilizing a flexible sheath in forming the medical device, manipulation and operation of the endoscope or other medical instrument is not compromised. Accordingly, not only can the medical devices facilitate operation of the medical instrument, but navigation deeper within the gastrointestinal tract via a natural bodily opening is possible. At the same time, the medical devices are easy to deploy and provides a secure engagement and fluidic seal with the internal bodily opening in the tissue that can prevent unwanted travel of bacteria laden fluids. The medical devices, systems, and methods provide reliable and safe access to an internal bodily opening via an external orifice such as a natural orifice.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for forming a pathway from an external orifice to a bodily opening defined by tissue of an internal bodily lumen, the medical device comprising:
    a flexible sheath having a longitudinal length suitable for forming the pathway, the flexible sheath having a distal portion that is collapsible; and
    an expandable frame connected to the distal portion of the sheath, the expandable frame operable between a collapsed configuration and an expanded configuration, the expandable frame expanding radially from the collapsed configuration to the expanded configuration;
    the expandable frame including a first cage having a proximal segment and a distal segment connected together by intermediate hinges, the proximal segment connected to the flexible sheath, the distal segment projecting distally beyond the distal portion of the flexible sheath;
    the distal segment rotating radially outwardly relative to the proximal segment about the intermediate hinges when the expandable frame expands radially from the collapsed configuration to the expanded configuration.

2. The medical device of claim 1, wherein the proximal and distal segments of the first cage are each defined by a plurality of struts having proximal and distal ends, the struts of the proximal segment connected together at their proximal ends by proximal hinges, the struts of the distal segment connected together at their distal ends by distal hinges, the plurality of struts rotating relative to one another about the proximal and distal hinges to permit the proximal and distal segments of the first cage to expand radially from the collapsed configuration to the expanded configuration.

3. The medical device of claim 2, wherein the plurality of struts are bent between their proximal and distal ends to define the intermediate hinges.

4. The medical device of claim 2, wherein pairs of struts are connected at their distal ends to define arms.

5. The medical device of claim 4, wherein each pair of struts criss-crosses proximate the intermediate hinges.

6. The medical device of claim 2, wherein the first cage and the plurality of struts are formed by a single wire bent into a configuration defining the proximal segment, the distal segment, and the intermediate hinges.

7. The medical device of claim 6, wherein the ends of the single wire are joined together to form a continuous path.

8. The medical device of claim 1, wherein the distal segment of the first cage is angled about 45 degrees to about 90 degrees relative to the proximal segment of the first cage in the expanded configuration.

9. The medical device of claim 1, wherein the distal segment of the first cage is angled about 75 degrees relative to the proximal segment of the first cage in the expanded configuration.

10. The medical device of claim 1, wherein the expandable frame has a longitudinal length substantially shorter than the longitudinal length of the flexible sheath.

11. The medical device of claim 1, further comprising a second cage connected to the distal portion of the flexible sheath and positioned proximally to the first cage, the second cage having a cylindrical shape in the expanded configuration.

12. The medical device of claim 1 wherein the expandable frame exerts a radially outward force on the sheath in their respective expanded configurations.

13. The medical device of claim 12, wherein the radially outward force is sufficient to affix the distal end of the sheath to the tissue.

14. The medical device of claim 1, wherein the proximal and distal segments of the first cage are formed by a wire, the intermediate hinge defined by a bend in the wire between the proximal and distal segments when the distal segment is rotated radially outwardly relative to the proximal segment.

15. A medical device for forming a pathway from an external orifice to a bodily opening defined by tissue of an internal bodily lumen, the medical device comprising:
   a flexible sheath having a length suitable for forming the pathway, the flexible sheath having a distal portion that is collapsible; and
   an expandable frame connected to the distal portion of the sheath, the expandable frame operable between a collapsed configuration and an expanded configuration, the expandable frame expanding radially from the collapsed configuration to the expanded configuration;
   the expandable frame including a first cage having a proximal segment and a distal segment connected together by intermediate hinges, the proximal segment connected to the flexible sheath, the distal segment projecting distally beyond the distal portion of the flexible sheath, the proximal and distal segments of the first cage each defined by a plurality of struts having proximal and distal ends, the struts of the proximal segment connected together at their proximal ends by proximal hinges, the struts of the distal segment connected together at their distal ends by distal hinges, the plurality of struts rotating relative to one another about the proximal and distal hinges to permit the proximal and distal segments of the first cage to expand radially from the collapsed configuration to the expanded configuration, wherein the distal ends of the plurality of struts define a plurality of loops;
   the distal segment rotating radially outwardly relative to the proximal segment about the intermediate hinges when the expandable frame expands radially from the collapsed configuration to the expanded configuration.

16. The medical device of claim 15, further comprising a suture extending through the plurality of loops and proximally through the flexible sheath.

17. The medical device of claim 16, wherein the suture includes a distal end forming a suture loop located between the plurality of loops, a proximal end of the suture passing through the plurality of loops and through the suture loop and then proximally through the flexible sheath.

18. The medical device of claim 16, further comprising an elongate tubular member extending through the flexible sheath, the elongate tubular member slidably receiving the suture, the elongate tubular member having a length greater than the length of the flexible sheath.

19. A method for accessing a bodily opening defined by tissue of an internal bodily lumen via an external orifice, the method comprising:
   providing a medical device comprising an expandable frame and a flexible sheath, the flexible sheath having a distal portion that is collapsible, the expandable frame connected to the distal portion of the sheath, the expandable frame operable between a collapsed configuration and an expanded configuration, the expandable frame expanding radially from the collapsed configuration to the expanded configuration, the expandable frame including a first cage having a proximal segment and a distal segment connected together by intermediate hinges, the proximal segment connected to the flexible sheath, the distal segment projecting distally beyond the distal portion of the flexible sheath, the distal segment rotating radially outwardly relative to the proximal segment about the intermediate hinges when the expandable frame expands radially from the collapsed configuration to the expanded configuration;
   delivering the distal end of the sheath and a portion of the expandable frame within the bodily opening while the expandable frame is in its collapsed configuration;
   operating the expandable frame to its expanded configuration such that the distal end of the sheath is placed in contact with the interior of the bodily opening formed in the bodily wall and the distal segment of the first cage rotates radially outwardly relative to the proximal segment, the distal segment located distally beyond the bodily opening and the bodily wall.

20. The method of claim 19, wherein the medical device further comprises a suture attached to distal ends of the distal segment of the first cage, and further comprising the steps of,
   introducing an elongate tubular member through the flexible sheath to a position where a distal end of the elongate tubular member is positioned distally beyond the distal segment, and
   retracting the suture proximally to rotate the distal segment radially inwardly relative to the proximal segment such that the distal segment is distal to the proximal segment.

21. The method of claim 19, wherein the sheath is pressed against the interior of the bodily opening to create a fluidic seal.

* * * * *